(12) United States Patent
Mueller-Enoch et al.

(10) Patent No.: US 8,153,676 B2
(45) Date of Patent: Apr. 10, 2012

(54) USE OF COMPOUNDS OF FORMULA A-R-XO PHARMACEUTICALLY ACCEPTABLE SALTS THEREOF FOR PRODUCING A PHARMACEUTICALLY PREPARATIONS

(76) Inventors: Dieter Mueller-Enoch, Dornstadt (DE); Thomas Haehner, Dornstadt (DE)

( * ) Notice: Subject to any disclaimer, the term of this patent is extended or adjusted under 35 U.S.C. 154(b) by 98 days.

(21) Appl. No.: 12/298,179

(22) PCT Filed: Apr. 27, 2007

(86) PCT No.: PCT/DE2007/000768
§ 371 (c)(1),
(2), (4) Date: Mar. 13, 2009

(87) PCT Pub. No.: WO2007/124734
PCT Pub. Date: Nov. 8, 2007

(65) Prior Publication Data
US 2009/0191262 A1    Jul. 30, 2009

(30) Foreign Application Priority Data
Apr. 28, 2006  (DE) .................. 10 2006 019 906

(51) Int. Cl.
| | | |
|---|---|---|
| A01N 43/50 | (2006.01) | |
| A61K 31/415 | (2006.01) | |
| C07D 233/54 | (2006.01) | |
| C07D 233/60 | (2006.01) | |

(52) U.S. Cl. ..................................... 514/399; 548/341.1
(58) Field of Classification Search .................. 514/399; 548/341.1
See application file for complete search history.

(56) References Cited

U.S. PATENT DOCUMENTS
2002/0183333 A1 * 12/2002 Shah et al. ............... 514/255.04

FOREIGN PATENT DOCUMENTS
| DE | 33 23 264 | 1/1984 |
|---|---|---|
| DE | 10 2004 052 697 A1 | 4/2006 |
| EP | 0 567 653 | 11/1993 |
| GB | 2 016 452 | 9/1979 |
| WO | 2006 045298 | 5/2006 |

OTHER PUBLICATIONS

Eshima et. al., CAS STN abstract, 1988.*
Blume et. al., Biochimica et Biophysica Acta, 1990, Elsevier, vol. 1029, pp. 91-97.*
Lu, et al; "Heme-coordination analogs of lauric acid as inhibitors of fatty acid ω-hydroxylation" Archives of Biochemistry and Biophysics, vol. 336, No. 1, Jan. 1, 1997, pp. 1-7.
Noble, et al; "Imidazolyl carboxylic acids as mechanistic probes of flavoeytochrome P-450 BM3"; Biochemistry, vol. 37 No. 45, 1998.
Bradley et al; "Relationships among cytotoxicity, lysosomal breakdown, chromosome aberrations, and DNA double-strand breaks". Mutat Res. Sep. 1987;189(1):69-79.
Cabantchik et al; "Effects of lysosomotropic detergents on the human malarial parasite plasmodium falciparum in in vitro culture"; Biochemical Pharmacology, vol. 38, No. 8, pp. 1271-1277, 1989.
Wilson et al, "Reduced cytotoxicity of the lysosomotropic detergent N-dodecylimidazole after differentiation of HL60 promyelocytes"; Cancer Res. Feb. 1, 1989;49(3):507-10.
Forster et al; "The effect of lysosomotropic detergents on the permeability properties of the lysosome membrane". Biochimica et Biophysica Acta. Jun. 22, 1987;924(3):452-7.
Wilson et al, "The role of lysosomal enzymes in killing of mammalian cells by the lysosomotropic detergent N-dodecylimidazole". J Cell Biol. May 1987;104(5):1223-9.

* cited by examiner

*Primary Examiner* — Sreeni Padmanabhan
*Assistant Examiner* — Sarah Pihonak
(74) *Attorney, Agent, or Firm* — Norris McLaughlin & Marcus. P.A.

(57) ABSTRACT

The invention relates to a compound of formula A-R—X or pharmaceutically acceptable salts thereof which can be used for producing a pharmaceutical preparation suitable for preventing or treating cancerous diseases, pathological consequences of alcohol abuse, viral hepatitis, steatohepatitis, acute and chronic pancreatitis, toxic renal diseases, hepatic insulin resistance in diabetes mellitus, hepatic damage in Wilson's disease and sideroses and/or ischaemic reperfusion damage, as an antidote against environmental toxins and medicament intoxication in order to extend the resistance time of medicaments in organisms, or for combating toxic side effects in the administration of chemotherapeutics. In the formula R is an aliphatic or aromatic $C_6$- to $C_{40}$-hydrocarbon radical which has a hydrophilic end A, and X is a radical having at least one free electron pair of a carbon or heteroatom and/or π-electrons.

3 Claims, 4 Drawing Sheets

Figure 1

| Aliphate | Heme-binding group | Structural formula | Designation |
|---|---|---|---|
| Fatty acid | Ethinyl group | | 17-octadecinyl acid |
| Alkanol | Imidazole | | 12-imidazolyl-1-dodecanol |
| Alkane | Imidazole | | 1-imidazolyl-dodecane |

Table 1: Examples of the imidazolized and/or ethinylated aliphates of the invention.

Figure 2

| Aliphate | Heme-binding group | Hydrophilic residue | Structural formula | Designation |
|---|---|---|---|---|
| Alkinol | Ethinyl group | phosphatidylcholine | | 17-octadecinyl-1-phosphatidylcholine |
| Alkanol | Imidazole | phosphatidylcholine | | 12-imidazolyl-dodecanol-1-phosphatidylcholine |
| ω-1-alkinyl residue | Ethinyl group | sphingosine head (1,3-dihydroxy-2-aminopropyl residue) | | 17-ethinyl-sphingosine |
| Sphingosine-hydrocarbon residue | Ethinyl group | 1,3-dihydroxy-2-N-formylamino-propyl residue | | 17-ethinyl-N-formyl-sphingosine |

Table 2: Examples of the inventive imidazolized and/or ethinylated aliphates, which are modified with a hydrophilic residue.

Figure 3

| Aliphatic residue | Hydrophilic residue | Structural formula |
|---|---|---|
| 2,17-octadecinyl acid | Serine residue | |
| 1. 12-imidazolyl-1-dodecanoic acid | Glycerol residue | |
| 2. 12-imidazolyl-1-dodecanoic acid | | |
| 3. 12-imidazolyl-1-dodecanoic acid | | |

Table 3: Examples of imidazolized and/or ethinylated glycerides of the invention.

Figure 4

| Aliphatic residue | Hydrophilic residue | Structural formula |
|---|---|---|
| 1. ethinylated fatty acid<br>2. ethinylated fatty acid | Phosphatidylserine-sn-3-glyceride | |
| 1. imidazolized fatty acid<br>2. imidazolized fatty acid | Phosphatidylcholine-sn-3-glyceride | |
| 1. palmitic acid<br>2. 12-imidazolyl-1-dodecanoic acid | Phosphatidylcholine-sn-3-glyceride | |

Table 4: Examples of imidazolized and/or ethinylated phosphoglycerides of the invention.

USE OF COMPOUNDS OF FORMULA A-R-XO PHARMACEUTICALLY ACCEPTABLE SALTS THEREOF FOR PRODUCING A PHARMACEUTICALLY PREPARATIONS

This application is a 371 of PCT/DE2007/000768, filed Apr. 27, 2007, which claims foreign priority benefit under 35 U.S.C. §119 of the German Patent Application No. 10 2006 019 906.5 filed Apr. 28, 2006.

The invention relates to the use of compounds of the formula A-R—X or their pharmaceutically acceptable salts for producing a pharmaceutical preparation for preventing or treating diseases and/or undesired conditions, in particular in humans. Moreover, the invention relates to such preparations themselves.

Excessive alcohol consumption for a prolonged period of time frequently leads to a liver disease—the so-called fatty liver—which can further develop into an inflammation of the liver or rather hepatitis and to cirrhosis of the liver in the late stage. Hence, the risk and the degree of the respective liver damage is a direct function of the amount and the duration of the alcohol consumption, so that the risk varies from individual to individual. An alcohol induced inflammation of the liver (alcohol hepatitis) is a disease that may be life threatening under some circumstances and is accompanied by fever, jaundice as well as an increase in the white blood cells. Such alcohol induced inflammations of the liver are curable by total abstinence of alcohol, except for scars in the case of cirrhosis of the liver.

Besides this alcohol-induced so-called fatty liver hepatitis or alcoholic steatohepatitis (ASH), hepatitises also develop in persons, who do not indulge in alcohol abuse or do not consume any alcohol at all. Such hepatitises are induced, for example, by environmental toxins, for example, when working in painting plants and/or also induced by prescription drugs.

It is known that oxidation processes in the metabolic process take place with the aid of cytochromes. Cytochromes are a plurality of different enzymes, the active center of which exhibits a heme structure. It catalyzes in a plurality of oxidation and hydroxylation reactions the transfer of electrons to an acceptor.

For example, the cytochromes of the P450 family (CYP 450) play an important role. In this case it involves monooxygenases, which are ubiquitous and belong to the most important enzymes of the metabolism of hydrophobic exogenous substances and of the modification of hydrophobic hormones, the steroids.

One of the main tasks of the cytochrome P450 enzyme is to solubilize exogenous substances by hydroxylation and in this way to deliver them to the renal excretion. Therefore, the cytochrome P450 enzymes play an important role in the detoxification process.

It is estimated that approximately half of all current drugs are hydroxylated by the cytochrome P450 enzymes of the liver. Therefore, the retention time of many drugs in the body is significantly reduced to some extent by the activity of the cytochrome P450 enzymes. In mammals the predominant amount of cytochrome P450 is found in the liver, because the liver is the central detoxifying organ. The cytochrome P450 is usually present in the combined state on the membrane of the endoplasmic reticulum.

Cytochrome P450 enzymes also play a key role in promoting the resistance of insects to insecticides and the resistance of plants to herbicides.

In its basic structure cytochrome P450 exhibits a six coordinated heme group, where a reaction of the following structure

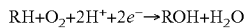

$$RH + O_2 + 2H^+ + 2e^- \rightarrow ROH + H_2O$$

is catalyzed. At the same time, the two electrons, which are necessary for this reaction, are made available—for example, by NADPH cytochrome P450 reductase—which are associated with the enzyme complex. In this way cytotoxic, reactive oxygen species (ROS) are produced, inter alia, at P450.

It is known that both alcohol consumption and non-alcoholic fatty liver hepatitis and pancreatitis induce the synthesis of cytochrome P450 2E1. The function and mechanism of action of this isoform, which is much different from other cytochromes, is described, for example, by M. H. Wang et al. in Archives of Biochemistry and Biophysics, (1995), Vol. 317, pages 299 to 304. According to this article, the enzyme exhibits an approximately 15 Å long duct, at the end of which is the reactive center with a heme ring exhibiting a central iron atom.

For a long time it has been suspected that even chemotherapeutic agents, such as those used in the therapy of cancer, are decomposed by the cytochrome P450 enzymes.

However, a recent article by Jiang et al. ("Cytochrome P450 2J2 Promotes the Neoplastic Phenotype of Carcinoma Cells and is Up-regulated in Human Tumors" in Cancer Res. 2005, 65: 4707-4715) revealed for the first time that the cytochrome P450 can even have a cancer promoting effect.

It was demonstrated that the gene expression of cytochrome P450 2J2 is up-regulated in human tumors. Cytochrome P450 2J2 is an epoxygenase, which converts the substrate arachidonic acid into four different isomeric epoxyeicosatrienoic acids (EET). Furthermore, the study showed that EETs exhibit an apoptosis-inhibiting effect, because they protect the tumor cells against the effect of the tumor necrosis factors, and in this way increase the lifespan of the cancer cells. Moreover, they promote the mitosis as well as the proliferation of tumor cells.

Similarly it could be demonstrated that EETs promote the angiogenesis—that the formation of new blood vessels. This process plays an important role in the growth of tumors (Pozzl A. et al. "Characterization of 5, 6 and 8, 9 Epoxyeicosatrienoic Acids (5, 6 and 8, 9 EET) as Potent in "Vivo Angiogenic Lipids", J. Biol. Chem. Vol. 280. pp. 27138-27146, 2005).

On the other hand, the article by Schattenberg et al. ("Hepatocyte CYP2E1 overexpression and steatohepatitis lead to impaired hepatic insulin signaling" in J. Biol. Chem. 2005; Vol. 280, pp. 9887-9894) links for the first time an overexpression of cytochrome P450 with diabetes.

Müller-Enoch et al. describe in Z. Naturforsch. (2001) 56c, pages 1082-1090 the inhibiting of cytochrome P450 2B1 in rats by means of lysophosphatidylcholines, lysophosphatidylinositol as well as arachidonic and oleinic acids and/or by monoacylglycerols, monooleylglycerols, and monopalmitoylglycerols.

Furthermore, T. Haehner, D. Müller-Enoch et al. in Z. Naturforschung (2004) 59c, pages 599-605 describe the influence of single chain lipid molecules on the activity of the isoform cytochrome P450 2B1 in rats.

The object of the invention is to provide means for producing a pharmaceutical preparation, which is suitable for preventing or treating cancerous diseases, pathological sequelae of alcohol abuse, viral hepatitis, steatohepatitis, acute and chronic pancreatitis, toxic renal disorders, hepatic insulin resistance in diabetes mellitus, liver damage associated with Wilson's disease and sideroses and ischemic reperfusion damage, for use as an antidote to environmental toxins and prescription drug intoxication, for prolonging the retention time of drugs in the organism, or for combating toxic side effects on administration of chemotherapeutic agents.

This object is achieved with a compound having the features defined in the claims.

In particular, it was found surprisingly that the aforementioned diseases can be treated with such compounds. These compounds inhibit the formation of reactive oxygen species (ROS), in particular, the oxygen radicals, like the superoxidants ($O_2^{\circ-}$) as well as hydrogen peroxide ($H_2O_2$), which are consumed in a direct redox reaction, at the cytochrome P450, in particular, at the isoforms of the genetic family 2, especially 2E1, as well as 2J2.

Similarly it was found that this compound inhibits the conversion of arachidonic acid into isomeric epoxyeicosatrienoic acids. Furthermore, it was shown that even the hydroxylation of exogenous substances can be inhibited upon administration of such a compound.

The compounds, which are used according to the invention, exhibit the formula

A-R—X.

As an alternative, their pharmaceutically acceptable salts can also be used.

In the formula R stands for an aliphatic or aromatic hydrocarbon residue, which has preferably 6 to 40 carbon atoms and exhibits, in particular, a terminal residue A, which is hydrophilic or hydrogen; and X stands for a residue exhibiting at least one free electron pair of a carbon or heteroatom and/or π electrons. The residue R is, in particular, lipophilic.

BRIEF DESCRIPTION OF THE DRAWINGS

The invention will now be described in greater detail with reference to the drawings, wherein:

FIG. 1 is a table listing examples of the imidazolized and/or ethinylated aliphates of the invention;

FIG. 2 is another table listing examples of the inventive imidazolized and/or ethinylated aliphates, which are modified with a hydrophilic residue;

FIG. 3 is another table listing examples of imidazolized and/or ethinylated glycerides of the invention; and FIG. 4 is another table listing examples of imidazolized and/or ethinylated phosphologycerides of the invention.

Usually the residue R is an alkyl residue. Thus, it may be straight chained or branched, exhibit single bonds, double bonds or triple bonds and may be substituted. Usually it exhibits an aliphatic backbone having 6 to 26, in particular 8 to 22 carbon atoms. Practical are hydrocarbon chains having a backbone of 10 to 15, in particular 10 to 13 carbon atoms. If R is an alicyclic or aromatic hydrocarbon residue, which may be condensed and/or may be substituted lipophilically, then it usually exhibits at least 5 and/or 6 and at most 40 and/or at most 25 carbon atoms.

Other practical minimum lengths are 7 and/or 8 C atoms; and other practical maximum lengths are 22 and/or 20 C atoms.

Practical residues X are heterocycles as well as alkinyl residues. The heterocycles are heterocycles, which contain, in particular, nitrogen, oxygen and/or sulfur, The heterocycles may be aromatic and/or non-aromatic and usually exhibit 5 or 6 ring atoms. In appropriate cases X may also be a condensed heterocycle. For example, such heterocycles are imidazole, pyrrole, pyrazole, pyridine, pyrazine, indole, isoindole, indazole. Preferred heterocycles are rings, which exhibit 6 and particularly 5 atoms and have one, two or three heteroatoms. Additional suitable heterocycles are, for example, thiazoles, triazoles, furans.

Preferred alkynes exhibit the structure —C≡C—$R_{12}$, where $R_{12}$ is a hydrogen or an optionally substituted $C_1$ to $C_{15}$ and/or maximally $C_{10}$ alkyl residue, which in turn may exhibit optionally double or triple bonds. Usually, however, $R_{12}$ exhibits maximally 5, in particular maximally 3 C atoms. In an additional practical embodiment of the invention, the residue X denotes, for example, primary, secondary and tertiary amines,
substituted or non-substituted diazo functions, such as hydrazines and hydrazones,
nitrile, isonitrile,
S-containing functional groups, such as thiocyanates and isothiocyanates, alkyl sulfides, sulfoxides, thiol groups,
methylene dioxy function,
alkyl ether and alkyl thio ether.

The residues X are expediently residues, which coordinate with the prosthetic heme group.

The hydrophilic terminus A of the molecule, which is to be used according to the invention, may be any pharmaceutically suitable hydrophilic function and, in particular an —OH, —COOH, a phosphate, phosphate ester, sulfate group, an amino group, an SH, as well as an amino acid or a polyalcohol, a carnitine (γ-N-trimethylamino-β-hydroxy-butyric acid), sphingosine head (1,3-dihydroxy-2-amino-propyl residue). If A is hydrogen, then A is not a hydrophilic end, but this compound can also be used as an inventive pharmaceutical preparation. Preferred amino acids are, in particular, those having positively or negatively charged residues, such as lysine, arginine, histidine, asparaginic acid, glutamic acid, glutamine, asparagine, homocysteine, serine, homoserine and/or citrulline. Preferred polyalcohols are, in particular, glycerol. Both glycerol and also the sugars may be optionally substituted. A practical substitution is, for example, the exchange of an OH group with an amino or SH group, respectively a phosphate or sulfate group. In an especially expedient embodiment A is a glycerol residue of the formula

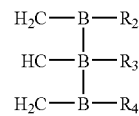

where at least one of the residues $R_2$ to $R_4$ is the above defined residue RX; and B is oxygen, sulfur, selene or selenate, an amino group, a phosphate or sulfate group. In another inventive embodiment an additional residue of $R_2$ to $R_4$ is a phosphatidylcholine residue, a phosphatidylethanolamine residue, a phosphatidylserine residue, or a phosphatidylinositol residue. Other suitable residues are, for example, the already aforementioned amino acids, in particular, those having positively or negatively charged residues.

In the case of 1,2-diacyl-sn-glycerol-3-phosphoric acid derivatives, the inventive application also comprises the basic structure of the cephalins, ceramides, lecithins and corresponding phospholipids, which exhibit a terminus X, as defined above.

Unbranched, saturated and non-substituted representatives X—R or $BR_{2-4}$ exhibit, for example, the following formulas:

alkanol residue: HO—$CH_2$—$(CH_2)_a$—X      a)

alkyl sulfate residue: $^-O_3SO$—$CH_2$—$(CH_2)_a$—X      b)

alkyl-CoA residue: CoA-S—CO—$(CH_2)_a$—X  c)

alkanoic acid residue: HOOC—$(CH_2)_a$—X  d)

where a denotes preferably at least 6 and, in particular, at least 7. Especially preferred a is at least 8; and 9 is very especially preferred. The preferred maximum values for a are 40, in particular 26, where 22, in particular 12, are preferred. 11 and especially 10 are especially preferred.

The corresponding formulas for branched, unsaturated or substituted representatives may be easily deduced by the person skilled in the art and, hence, do not need any separate presentation.

Additional examples of aliphatic residues R are, for example, a dodecane residue, an octadecanol residue, an undecanylsulfate residue, a palmityl-CoA residue or a lauric acid residue.

In an alternative embodiment π electrons of the residue X are, in particular, those from olefinic, in particular acetylenic double and/or triple bonds, which are usually terminal. Especially expedient residues are an imidazole residue, bound by way of a nitrogen atom, or an ethinyl residue (—C≡C—).

It has been demonstrated that in situations, in which the above defined compounds, in particular those that contain an imidazolized or ethinylated fatty acid as X and those—such as 17-octadecinyl-1-acid—which have proved to be especially effective in vitro, are used in accordance with the invention, the retention time of many active ingredients in the blood can be significantly prolonged by replacing the carboxy terminus of such a molecule, for example, with a sulfate residue, or one adjacent to the carboxy terminus—that is, 1-3 C atoms (α, β, γ position)—of the aliphatic backbone is substituted through the addition of 2 methyl groups or an aliphatic or aromatic ring. In this way even the in vivo activity is improved in conformity with the in vitro activity.

Thus, for example, 2,2-dimethyl-11-dodecinyl acid and 10-undecinyl-sulfate exhibit in vitro a comparably high inhibition of cytochrome P450 activity, like 10-undecinyl acid, whereas they are far superior in vivo to the latter.

Preferably it is provided at the same time that the length of the aliphatic backbone comprises 6 to 26, in particular 9 to 20 and/or 19, carbon atoms, when R1 is an imidazole residue. One representative of this preferred group is, for example, the 12-imidazolyl-dedecanol or the 1-imidazolyl-dedecane. With respect to the structural formulas of these and other substances reference is made to the attached drawings.

Furthermore, an inventive embodiment provides that the length of the aliphatic backbone comprises 6 to 26 carbon atoms, if R1 is an ethinyl residue. One representative of this preferred group is, for example, 17-octadecinyl-1-acid.

According to an additional embodiment, the length of the aliphatic backbone comprises 9 to 13 carbon atoms, if R1 is an ethinyl residue. Representatives of this preferred group are, for example, 2,2-dimethyl-11-dodecinyl acid, 10-undecinyl-sulfate, 10-undecinyl acid or 10-undecinol.

These compounds exhibit a number of advantages. First of all, they are not directly accessible to enzymes of the β-oxidation metabolic process and are, therefore, not immediately metabolized by said enzymes.

Phosphoglycerides and triglycerides (according to the above definition), which are substituted with a residue of the formula —R—X, for example an ethinylated or imidazolized aliphate residue, at two sites of the glycerol residue, are hydrolyzed in the intestine following resorption, and in particular in such a manner that one of the two aliphatic residues is split off. In this way ethinylated and/or imidazolized monoglycerides are produced. Owing to their solubility, said monoglycerides are also called lysolipids and are conveyed to the active sites in the body with the aid of lipoproteins, thus non-covalent aggregates composed of lipids and proteins, which form micelle-like particles and serve to transport water-insoluble lipids in the blood.

The same also applies, moreover, to ethinylated and/or imidazolized monoglycerides (according to the above definition) that were already administered as such.

Since specific pathogenic tissues, such as tumors, have a high energy turnover and promote their own vascularization by releasing growth factors (VEGF, PDGF), the lipoproteins, loaded with the said ethinylated and/or imidazolized monoglycerides, migrate with the blood stream preferably into these tissues. Thus, the "packaging" of ethinylated and/or imidazolized aliphates in the form of lysolipids makes it possible to convey specifically said lysolipids into the said pathogenic tissues.

In the inventive application, the compounds show an effect in cancer therapy. Among other things, the conversion of arachidonic acid into epoxyeicosatrienoic acids is inhibited. The latter promote the cell division and proliferation and inhibit the apoptosis of tumor cells. Similarly the application of such a compound inhibits the hydroxylation of chemotherapeutic agents that ultimately leads to the excretion of said chemotherapeutic agents and, thus, to their inactivation. Hence, such a compound can be used for a direct as well as for an adjuvant tumor therapy. For this reason the aforementioned embodiment, which makes possible a targeted transport into the pathogenic tissue, promises to be especially successful.

Furthermore, the invention provides a pharmaceutical preparation, containing an inventive compound in a pharmaceutically acceptable carrier.

In addition, possible indications for an inventive compound and/or its pharmaceutical preparation lie in the treatment of the sequelae of alcohol abuse. They are, in particular, liver damage and also other alcohol induced inflammatory processes. In addition to the liver damage that is simply alcohol induced, nutrition-induced and endocrine factors, such as obesity as well as diabetes mellitus and hyperlipidemia, also cause, independently of alcohol, serious liver damage, which may range over fatty liver hepatitis (non-alcoholic steatohepatitis=NASH) as far as up to and including cirrhosis of the liver. Such alcoholic and non-alcoholic fatty liver diseases are often accompanied by a viral infection of the liver. In this case the consequence may be a very fast progression of the disease. It has been demonstrated that all of the aforementioned diseases and/or their causes or their sequelae are treatable with the inventive compounds.

It has also been found that these substances are quite appropriate for treating inflammations of the pancreas. Such inflammations and/or pancreatitis may be induced not only by alcohol abuse but also by toxic substances. They include, in particular, environmental toxins, like occupational chemicals or also prescription drugs. Even viral infections or endocrine factors of a metabolic origin may cause such inflammations of the pancreas. In all cases reactive oxygen species are involved in the development of the disease and in the progression of the disease.

The inventive pharmaceutical preparation has also proven to be appropriate for the treatment of diabetes mellitus—both type 1 and type 2 diabetes mellitus.

Even toxic renal disorders as well as other disorders, such as those induced by the side effects on the administration of chemotherapeutic agents, in particular cytotoxins, like metal complexes like cisplatinum, carboplatinum, titanocendichloride or gold complexes, are to be treated with the inventive drug. In this respect it has been demonstrated in particular that the organotoxicity of metal complexes or also other toxic mediums, like halogenated hydrocarbons and, in particular, both monohalogenated and polyhalogenated hydrocarbons, among these also the vapor anesthesias of the halothane type, as well as the corresponding aromatic hydrocarbons, nitrosamines, acrylamide or drugs, like paracetamol, methotrexate, isoniacide or aminoglycoride antibiotics or X-ray contrast mediums, can be suppressed. Therefore, the inventive drug is also suitable for the treatment of organotoxicity caused by environmental toxins, in particular as an antidote thereto, in organs, like the liver, kidney, central nervous system, pancreas, etc.

Hence, it also makes it possible, for example, to increase the dose of cytostatic drugs in the treatment of cancer and, against this background, may also raise, as an adjuvant therapy, the prospects of success in chemotherapy.

It has proven to be quite especially suitable for preventing damage, resulting from the reperfusion of biological tissues, such as after an infarction of an organ, especially the heart, as well as the brain (cardiac infarction, stroke). Thus, for example animal experiments have demonstrated that such reperfusion damage contributes from 60 to 80% of the tissue destruction and/or that the spread of tissue necrosis can be reduced by this factor. For a long time it has been known that reperfusion damage is caused predominantly by the oxygen radicals, which are formed during the ischemia.

Thus, the inventive preparation is also especially suitable for preventing reperfusion damage in transplanted organs. Such organs are kept in a cooled nutrient solution until they are transplanted into the body of a new recipient. Following the transplant, the body fluids flow through these organs, after being connected to the circulatory system of the recipient, as a result of which reperfusion damage occurs. An administration of the inventive preparation before and during the storage as well as just before the implanting into the receiving organism may also solve this important transplant problem.

An accumulation of the transition metal iron (and/or copper in Wilson's disease) raises the potential of oxidative damage caused by cytochrome P450. Apart from excess iron in the sense of siderosis, it is known that in the case of ischemic reperfusion damage there is a significant increase in the intracellular concentration of free iron. An intracellular increase in iron is also induced by toxic compounds, such as cisplatinum or halogenated hydrocarbons or by viral hepatitises. Predominantly the liver is affected, but in the case, for example, of cisplatinum, which is excreted through the kidneys, the kidney is affected. The Fenton reaction shows the biochemical basis of oxidative damage caused by the transition metal iron (and/or copper in the case of Wilson's disease).

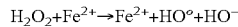

The $H_2O_2$ (redox potential +0.32 volts), produced within the framework of the cytochrome P450 reaction cycle, is converted into the very highly oxidizing hydroxyl radical $HO°$ (redox potential +2.31 volts.

An increase in the concentration of free iron within the framework of cisplatinum-induced nephropathy is described, for example, in an article by Baliga et al. ("Role of cytochrome P450 as a source of catalytic iron in cisplatin-induced nephrotoxicity", Kidney Int. 1998, Vol. 54, pp. 1562-1569). An increase in iron associated with ischemic reperfusion damage or viral hepatitis is described, for example, by Paller et al. ("Cytochrome P450 mediates tissue damaging hydroxyl radical formation during reoxygenation of the kidney", Proc. Natl. Acad. Sci., USA, 1994, Vol. 91, pp. 7002-7006) and/or by Chapoutot et al. (Liver iron excess in patients with hepatocellular carcinoma developed on viral C cirrhosis, Gut 2000, vol. 46, pp. 711-714).

The inventive substances have proven to be, in particular, inhibitors of human isoforms of the genetic family 2 of the cytochrome P450 and, in particular, the isoforms 2E1 and 2J2 and of the disorders, caused by them.

An especially practical embodiment of the invention provides that the pharmaceutical preparation be incorporated into the liposomes. Owing to the fact that the compounds, on which the preparation is based, exhibit long aliphatic residues, their incorporation into liposomes is a very suitable form of administration. Such liposomes are suitable for intravenous, intramuscular, intraperitoneal, percutaneous or also oral administration. An administration as an aerosol is just as suitable.

However, the inventive compounds may also be administered directly as such. In this case, too, the aforementioned types of administration are suitable.

METHODS OF SYNTHESIS

Several methods for synthesizing a wide array of inventive compounds are described below.

1. Synthesis of 12-imidizolyl-1-dodecanoic Acid a) 12-imidazolyl-1-dodecanoic acid is synthesized according to a method that is described in the article by Alternan et al. ("Fatty acid discrimination and omega-hydroxylation by cytochrome P450 4A1 and a cytochrome P4504A1/NADPH-P450 reductase fusion protein", Archives of Biochemistry and Biophysics 1995, Vol. 320, pp. 289-296).

To this end, 12-bromo-1-dodecanol is oxidized with Jones' reagent to form 12-bromo-1-dodecanoic acid. Then the white solid acid is esterified with diazomethane to form the corresponding methyl ester. The methyl ester is treated directly with imidazole and reacted at 80° C. for five hours until it forms 12-imidazolyl-1-dodecanoic acid methyl ester. The thick mass, which is obtained in this way, is split between water and dichloromethane; and the organic phase is dried over $Na_2SO_4$ and concentrated by evaporation. The oily residue is cleaned chromatographically on silica gel and then dissolved in a mixture of methanol and tetrahydrofuran (3:4), treated with $LiOH.H_2O$, and the mixture is heated under reflux for two hours. Following evaporation of the solvent, the white residue is dissolved again in water, extracted with dichloromethane, acidified to a pH 5-6, and extracted again with ethyl acetate. The ethyl acetate extract is dried over $Na_2SO_4$, filtered and concentrated by evaporation. The white solid is recrystallized from methanol/ether and yields 12-imidazolyl-1-dodecanoic acid.

b) 12-imidazolyl-1-dodecanol and 1-imidazolyldodecane are synthesized according to a method that is described in the article by Lu et al. ("Heme-coordinating analogs of lauric acid as inhibitors of fatty acid ω-hydroxylation", Archives of Biochemistry and Biophysics, 1997, Vol. 337, pp. 1-7).

To this end, the temperature of 12-bromo-1-dodecanol and imidazole in a molar ratio of 1:3 is raised to 80° C. for five hours. The raw product is divided between water and dichloromethane. The organic phase is dried over $Na_2SO_4$ and concentrated by evaporation. The 12-imidazolyl-1-dodecanol is recrystallized from benzene/n-hexane.

c) 1-imidazolyldodecane is produced from 1-bromododecane and imidazole in a molar ratio of 1:3 while stirring and heating at 85° C. The raw product is dissolved in dichloromethane and poured out three times with water. The organic phase is dried over $Na_2SO_4$, filtered and concentrated by evaporation. The oily evaporation residue is induced to crystallize from n-hexane and yields 1-imidazolyldodecane.

2. Synthesis of 12-imidazolyl-1-phosphatidylcholine

Phosphatidylcholine is reacted to form an O-phosphoryl isourea under acidic conditions in the presence of dicyclohexylcarbodiimide. 12-imidazolyl-1-dodecanol is added to the reaction mixture. This 12-imidazolyl-1-dodecanol attacks nucleophilically the phosphoryl group and forms with this phosphoryl group an ester bond, so that 12-imidazolyl-1-phosphatidylcholine is formed. In so doing, dicyclohexylurea settles out. In order for this reaction to succeed, 4-diethylaminopyridine is necessary as the catalyst.

The reaction mechanism is similar to that of the Steglich esterification, where dicyclohexylcarbodiimide is used, in order to esterify an organic acid with an alcohol.

3. Synthesis of 1-palmitoyl-2-imidazolyl-glyerco-3-phosphatidylcholine

The principle for the synthesis of a phosphatidylcholine-diglyceride, which carries an unmodified fatty acid and a labeled (that is, in the present case an ethinylated or imidazolized) fatty acid, is described by Eibl et al. ("Synthesis of labeled phospholipids in high yield," Methods Enzymol. 1983, vol. 98, pp. 623-632).

3a. Synthesis of 1,2-dipalmitoyl-3-benzyl-glyceride

To this end, 1,2-isopropylidene-sn-glycerol is dissolved in p-xylene and stirred with the addition of potassium-tert.-butylate and benzyl chloride. Upon completion of the reaction, water and diisopropyl ether are added in equal parts; and a phase separation is carried out. The 3-benzyl-sn-glycerol in the upper phase is obtained by evaporation and subjected to additional cleaning steps.

Then the cleaned 3-benzyl-sn-glycerol is dissolved with a fatty acid, for example palmitate, in carbon tetrachloride. With the addition of 4-diethylaminopyridine and dicyclohexylcarbodiimide, ester bonds are produced between the alcohol groups of the 3-benzyl-sn-glycerol and the carboxyl groups of the fatty acids, so that dicyclohexylurea settles out. This reaction mechanism is also called "Steglich esterification".

The precipitated dicyclohexylurea is removed; and the solvent is removed by evaporation. Following additional cleaning steps, the product 1,2-dipalmitoyl-3-benzyl-sn-glycerol is obtained.

3b. Synthesis of 1,2-dipalmitoyl-sn-glyceride 1,2-dipalmitoyl-3-benzyl-sn-glyceride is dissolved in tetrahydrofuran and hydrogenolyzed with elementary hydrogen in the presence of a catalyst (10% Pd/C). In so doing, the benzyl residue is substituted with a hydrogen atom; and 1,2-dipalmitoyl-sn-glyceride is produced.

3c. Phosphorylation of 1,2-dipalmitoyl-sn-glyceride

Phosphoryl trichloride is treated with triethylamine, dissolved in tetrahydrofuran, and stirred in ice. Then 1,2-dipalmitoyl-sn-glyceride, dissolved drop-by-drop in tetrahydrofuran, is added. The result is then 1,2-dipalmitoyl-sn-glyceride-3-phosphoryl dichloride.

Then triethylamine, dissolved in tetrahydrofuran is added once more; bromoethanol, dissolved drop by drop in tetrahydrofuran, is added; and the temperature is raised to 25° C. The result is then predominantly 1,2-dipalmitoyl-sn-glyceride-3-phosphoryl-bromoethyl ester-monochloride and just a small quantity of the corresponding di-bromoethyl ester as a side product.

This mixture is cleaned, cooled, treated with sodium carbonate and hexane and shaken. In so doing, the bond between the phosphate residue and the chloride is hydrolyzed. The resulting product is the sodium salt of 1,2-dipalmitoyl-sn-glyceride-3-phosphoryl-bromoethyl ester.

The sodium salts of 1,2-dipalmitoyl-sn-glyceride-3-phosphoryl-(N-butoxycarbonyl)ethanol amine ester and 1,2-dipalmitoyl-sn-glyceride-3-phosphoryl-(N-butoxycarbonyl) tert-butyl serine ester are isolated in an analogous manner.

3d. Hydrolyzation of 1,2-dipalmitoyl-sn-glyceride-3-phosphoalkyl Ester 1,2-dipalmitoyl-sn-glyceride-3-phosphoryl-bromoethyl ester or one of the aforementioned phosphoalkyl esters, which are presented as an alternative, is dissolved in a mixture of diethyl ether and distilled water, containing $CaCl_2.2H_2O$.

The pH is adjusted to 7.5 with the addition of a Palitzsch buffer. Then the enzyme phospholipase $A_2$ is added and stirred for 60 min. at 35° C. At the same time the ester bond at position 2 of the glycerol residue is hydrolyzed; and the resulting product is the corresponding 1-palmitoyl-sn-glyceride-3-phosphoalkyl ester, which carries an OH group at position 2, and a free fatty acid.

At this point the molecule that is obtained can be esterified specifically with a labeled fatty acid—for example, an imidazolized or ethinylated fatty acid—at position 2 of the glycerol residue. Similarly the phosphoalkyl ester can be re-esterified with a suitable alcohol—for example, choline, serine, ethanolamine or inositol—at position 3.

3e. Esterification with a Labeled Fatty Acid at Position 2

The obtained 1-palmitoyl-sn-glyceride-3-phosphoalkyl ester is dissolved in tetrachloromethane. An imidazolized or ethinylated fatty acid is added; and the mixture is stirred.

The fatty acid that is added may be, for example, 17-octadecinic acid, which is commercially available at Sigma Aldrich. Similarly it may be 12-imidazolyl-1-dodecanoic acid, which can be synthesized as described under 1.

Then a "Steglich esterification" is carried out again; 4-diethylaminopyridine and dicyclohexylcarbodiimide are added to the mixture. At the same time an ester bond is formed between the remaining OH group at the glycerol residue and the carboxyl group of the labeled fatty acid.

The precipitated dicyclohexylurea is removed; and the solvent is removed by evaporation. Following additional cleaning steps, 1-palmitoyl-2-acyl-sn-glyceride-3-phosphoalkyl ester is obtained as the product.

3f. Re-Esterification of the Phosphoalkyl Ester at Position 3 of the Glycerol Residue 1-palmitoyl-2-acyl-sn-glyceride-3-phosphoryl-bromoethyl ester is dissolved in chloroform. Then 2-propanol-trimethylamine is added. The reaction vessel is incubated at 50° C. Then the solvent is evaporated with nitrogen. The reaction product is cleaned; and in this way a labeled 1-palmitoyl-2-acyl-sn-glyceride-3-phosphatidylcholine is obtained.

In order to isolate the labeled 1-palmitoyl-2-acyl-sn-glyceride-3-phosphatidyl-serine, the labeled 1-palmitoyl-2-acyl-sn-glyceride-3-phosphoryl-(N-butoxycarbonyl)ethanolamine ester, which is isolated as aforementioned, is dissolved in $CH_2Cl_2$; and trifluoroacetic acid and perchloric acid are added. Then the mixture is stirred in the cold state and washed with water and methanol. Following a phase separation, the lower phase is extracted with $Na_2CO_3$ and evaporated. Following the addition of methanol, crystals form. These crystals are the labeled 1-palmitoyl-2-acyl-sn-glyceride-3-phosphatidyl-ethanolamine.

A similar method is used to isolate labeled 1-palmitoyl-2-acyl-sn-glyceride-3-phosphatidylserine. In this case the parent substance is 1-palmitoyl-2-acyl-sn-glyceride-3-phosphoryl-(N-butoxycarbonyl) tert-butyl serine ester, which is isolated as aforementioned.

Tables

The attached tables list a few examples of the inventive compounds.

Tables 1 to 3 show some examples of the compounds that are used according to the invention and exhibit the formula A-R—X, as disclosed in claim 1.

In this respect it is clear to the person skilled in the art that a plurality of other compounds can be subsumed under the said claims. Thus, the aliphatic residues may be straight chained or branched; exhibit single, double or triple bonds, and may be substituted, and exhibit an aliphatic backbone having 9 to 19 carbon atoms. Similarly the hydrocarbon backbone can be formed with alicyclic and/or aromatic hydrocarbons, so that in this case owing to the ring structures up to 40 carbon carbons may be necessary.

Suitable hydrophilic residues are also other alcohols, like inositol and ethanolamine and/or their glycerides.

Toxicity

The acute toxicity of 12-imidazolyl-1-dodecanol (substance 1) and 12-(1)-imidazolyl-dodecane (substance 2) was tested in male CD rats. For 12-imidazolyl-1-dodecanol the result was an LD50 (14 days) of 1,000 mg/kg, b.w., p.o.; and for 12-(1)-imidazolyl-dodecane an LD50 (14 days) of 1,000 mg/kg b.w., p.o.

| | |
|---|---|
| First intolerance reaction: | substance 1: 1,000 mg/kg b.w., p.o. |
| | substance 2: 500 mg/kg b.w., p.o. |
| No effect at the dose rate: | substance 1: 500 mg/kg b.w., p.o. |
| | substance 2: 250 mg/kg b.w., p.o. |

Determination of Antineoplastic Effect of 12-imidazolyl-1-dodecanol

To this end, four cancer cell lines were seeded into "24 well plates" and allowed to grow for 24 hours. Then a wide array of the concentrations of the test substance 12-imidazolyl-1-dodecanol, dissolved in DMSO, was added to the cell suspensions. The DMSO concentration in the cell medium was 0.01%. This DMSO concentration proved to be non-toxic in the control test; the cell counts were conducted after a four day incubation period. In all cases a strong inhibition of cancer cell proliferation was determined.

The following half maximum inhibitory concentrations—IC50 values—of 12-imidazolyl-1-dodecanol were determined:

| | |
|---|---|
| HepG2 (liver cells) | 50 nM |
| Panc-1 (pancreas cells) | 50 nM |
| PC-3 (prostate cells) | 50 nM |
| SW620 (large intestine cells) | 100 nM |

A high antineoplastic effect of the inhibitor was determined in all of the cancer cell lines.

Evaluation of the Cytotoxicity of 12-imidazolyl-1-dodecanol

The half maximum cytotoxicity of 12-imidazolyl-1-dodecanol was determined with the LDH cytotoxicity test.

In this respect the following values were measured:

| | |
|---|---|
| MRC-5 (lung fibroblast cells) = | 500 µM |
| Panc-1 (pancreas cells) = | 500 µM |

A comparison between the half maximum cytotoxicity of 500 µm and the half maximum inhibitory constant IC50=50 µM for Panc-1 revealed a differential factor of 10,000. Therefore, the conclusion can be drawn that 12-imidazolyl-dodecanol is a highly effective inhibitor of cancer cell proliferation with relatively low cytotoxicity.

In other words, the inventive substances have a wide therapeutic window.

Migratory Activity of hepG2 Cells Inhibited by 12-imidazolyl-1-dodecanol

Migration test conditions: HepG2 liver cancer cells were embedded in a collagen matrix. Thirty individual cells were inspected continuously by photographic means for 900 minutes. The average percentage of migrating cells was determined.

Result 1: Non-treated control HepG2 cells exhibit a mean migratory activity of 15%. With the addition of 1 µM or 10 µM 12-imidazolyl-1-dodecanol to the matrix medium, the migratory activity of the cells dropped by 50% or 75% respectively.

Result 2: Since HepG2 cells exhibit a strong expression of insulin receptors, the influence of insulin on the migratory activity was determined with and without 12-imidazolyl-1-dodecanol.

| HepG2 cells | Mean migratory activity |
|---|---|
| Control group | 15% |
| Addition of insulin (100 ng/ml) | 38% |
| Addition of insulin (100 ng/ml) and 12-imidazolyl-1-dodecanol (10 µl) | 15% |

Insulin produced a 2.5-times increase in the migratory activity. The active substance blocks this increase completely after 450 min. observation time (first half of the observation time). After 900 minutes (second half of the observation time), the increase is negative. The mean migratory activity is then 13% below that of the control group.

The invention claimed is:

1. The compound 12-imidazolyl-1-dodecanol or a pharmaceutically acceptable salt thereof.

2. A pharmaceutical composition comprising the compound or salt thereof according to claim 1 and a pharmaceutically acceptable carrier.

3. The pharmaceutical composition according to claim 2, which is incorporated into liposomes.

* * * * *